(12) United States Patent
Romero (10) Patent No.: US 9,248,272 B2
(45) Date of Patent: *Feb. 2, 2016

(54) SEGMENTED ELECTRODE LEADS FORMED FROM PRE-ELECTRODES WITH DEPRESSIONS OR APERTURES AND METHODS OF MAKING AND USING

(71) Applicant: BOSTON SCIENTIFIC NEUROMODULATION CORPORATION, Valencia, CA (US)

(72) Inventor: Daniel James Romero, Granada Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/286,797

(22) Filed: May 23, 2014

(65) Prior Publication Data

US 2014/0358207 A1     Dec. 4, 2014

Related U.S. Application Data

(60) Provisional application No. 61/829,918, filed on May 31, 2013, provisional application No. 61/981,606, filed on Apr. 18, 2014.

(51) Int. Cl.
*A61N 1/05*       (2006.01)
*A61N 1/36*       (2006.01)

(52) U.S. Cl.
CPC ............... *A61N 1/05* (2013.01); *A61N 1/0534* (2013.01); *A61N 1/3605* (2013.01); *Y10T 29/4922* (2015.01)

(58) Field of Classification Search
CPC ..... A61N 1/05; A61N 1/0534; A61N 1/3605; Y10T 29/4922
See application file for complete search history.

(56) References Cited

U.S. PATENT DOCUMENTS

| 4,602,624 A | 7/1986 | Naples et al. |
| 4,630,611 A | 12/1986 | King |

(Continued)

FOREIGN PATENT DOCUMENTS

| EP | 0580928 A1 | 2/1994 |
| EP | 0650694 B1 | 7/1998 |

(Continued)

OTHER PUBLICATIONS

U.S. Appl. No. 14/557,211, filed Dec. 1, 2014.

(Continued)

*Primary Examiner* — Rex R Holmes
(74) *Attorney, Agent, or Firm* — Lowe Graham Jones PLLC; Bruce E. Black (57) ABSTRACT

A pre-electrode for a stimulation lead includes a generally cylindrical body having an exterior surface, an interior surface, a proximal end, and a distal end. The body includes segmented electrodes disposed along the body in a spaced-apart configuration, connecting material coupling each of the segmented electrodes to one another and forming the exterior surface of the body, and cutouts defined between adjacent segmented electrodes. In some instances, the pre-electrode includes at least one depression in the exterior surface of the pre-electrode over one of the segmented electrode so that the pre-electrode is thinner at the depression than at immediately adjacent portions of the pre-electrode. In some instances, the pre-electrode includes at least one aperture extending into the body from the exterior surface and between two of the segmented electrodes with portions of the connecting material forming borders between the aperture and the proximal and distal ends of the pre-electrode.

20 Claims, 6 Drawing Sheets

(56) References Cited

U.S. PATENT DOCUMENTS

| | | | |
|---|---|---|---|
| 4,744,370 | A | 5/1988 | Harris |
| 5,000,194 | A | 3/1991 | van den Honert et al. |
| 5,135,001 | A | 8/1992 | Sinofsky et al. |
| 5,374,285 | A | 12/1994 | Vaiani et al. |
| 5,458,629 | A | 10/1995 | Baudino et al. |
| 5,522,874 | A | 6/1996 | Gates |
| 5,711,316 | A | 1/1998 | Elsberry et al. |
| 5,713,922 | A | 2/1998 | King |
| 5,800,350 | A | 9/1998 | Coppleson et al. |
| 5,843,148 | A | 12/1998 | Gijsbers et al. |
| 5,938,688 | A | 8/1999 | Schiff |
| 5,987,361 | A | 11/1999 | Mortimer |
| 6,018,684 | A | 1/2000 | Bartig et al. |
| 6,134,478 | A | 10/2000 | Spehr |
| 6,161,047 | A | 12/2000 | King et al. |
| 6,167,311 | A | 12/2000 | Rezai |
| 6,322,559 | B1 | 11/2001 | Daulton et al. |
| 6,510,347 | B2 | 1/2003 | Borkan |
| 6,556,873 | B1 | 4/2003 | Smits |
| 6,564,078 | B1 | 5/2003 | Marino et al. |
| 6,678,564 | B2 | 1/2004 | Ketterl et al. |
| 6,757,970 | B1 | 7/2004 | Kuzma et al. |
| 7,027,852 | B2 | 4/2006 | Helland |
| 7,047,084 | B2 | 5/2006 | Erickson et al. |
| 7,203,548 | B2 | 4/2007 | Whitehurst et al. |
| 7,292,890 | B2 | 11/2007 | Whitehurst et al. |
| 7,489,971 | B1 | 2/2009 | Franz |
| 7,668,601 | B2 | 2/2010 | Hegland et al. |
| 7,761,985 | B2 | 7/2010 | Hegland et al. |
| 7,822,482 | B2 | 10/2010 | Gerber |
| 7,840,188 | B2 | 11/2010 | Kurokawa |
| 7,848,802 | B2 | 12/2010 | Goetz |
| 7,856,707 | B2 | 12/2010 | Cole |
| 7,860,570 | B2 | 12/2010 | Whitehurst et al. |
| 7,974,705 | B2 | 7/2011 | Zdeblick et al. |
| 7,979,140 | B2 | 7/2011 | Schulman |
| 8,000,808 | B2 | 8/2011 | Hegland et al. |
| 8,019,440 | B2 | 9/2011 | Kokones et al. |
| 8,036,755 | B2 | 10/2011 | Franz |
| 8,041,309 | B2 | 10/2011 | Kurokawa |
| 8,099,177 | B2 | 1/2012 | Dahlberg |
| 8,225,504 | B2 | 7/2012 | Dye et al. |
| 8,295,944 | B2 | 10/2012 | Howard et al. |
| 8,321,025 | B2 | 11/2012 | Bedenbaugh |
| 8,359,107 | B2 | 1/2013 | Pianca et al. |
| 8,391,985 | B2 | 3/2013 | McDonald |
| 8,583,237 | B2 | 11/2013 | Bedenbaugh |
| 8,649,873 | B2 | 2/2014 | Moffitt et al. |
| 2001/0023368 | A1 | 9/2001 | Black et al. |
| 2002/0156513 | A1 | 10/2002 | Borkan |
| 2002/0183817 | A1 | 12/2002 | Van Venrooij et al. |
| 2005/0015130 | A1 | 1/2005 | Gill |
| 2005/0038489 | A1 | 2/2005 | Grill |
| 2005/0171587 | A1 | 8/2005 | Daglow et al. |
| 2006/0025841 | A1 | 2/2006 | McIntyre |
| 2006/0247697 | A1 | 11/2006 | Sharma et al. |
| 2007/0168007 | A1 | 7/2007 | Kuzma et al. |
| 2007/0203546 | A1 | 8/2007 | Stone et al. |
| 2007/0219551 | A1 | 9/2007 | Honour et al. |
| 2008/0077186 | A1 | 3/2008 | Thompson et al. |
| 2008/0103580 | A1 | 5/2008 | Gerber |
| 2008/0114230 | A1 | 5/2008 | Addis |
| 2008/0215125 | A1 | 9/2008 | Farah et al. |
| 2008/0255647 | A1 | 10/2008 | Jensen et al. |
| 2009/0204192 | A1 | 8/2009 | Carlton et al. |
| 2010/0030298 | A1 | 2/2010 | Martens et al. |
| 2010/0036468 | A1 | 2/2010 | Decre et al. |
| 2010/0076535 | A1 | 3/2010 | Pianca et al. |
| 2010/0077606 | A1 | 4/2010 | Black et al. |
| 2010/0082076 | A1 | 4/2010 | Lee et al. |
| 2010/0094387 | A1 | 4/2010 | Pianca et al. |
| 2010/0100152 | A1 | 4/2010 | Martens et al. |
| 2010/0268298 | A1 | 10/2010 | Moffitt et al. |
| 2010/0269338 | A1 | 10/2010 | Dye |
| 2010/0269339 | A1 | 10/2010 | Dye et al. |
| 2010/0287770 | A1 | 11/2010 | Dadd et al. |
| 2011/0005069 | A1 | 1/2011 | Pianca |
| 2011/0047795 | A1 | 3/2011 | Turner et al. |
| 2011/0056076 | A1 | 3/2011 | Hegland et al. |
| 2011/0077699 | A1 | 3/2011 | Swanson et al. |
| 2011/0078900 | A1 | 4/2011 | Pianca et al. |
| 2011/0130803 | A1 | 6/2011 | McDonald |
| 2011/0130816 | A1 | 6/2011 | Howard et al. |
| 2011/0130817 | A1 | 6/2011 | Chen |
| 2011/0130818 | A1 | 6/2011 | Chen |
| 2011/0131808 | A1 | 6/2011 | Gill |
| 2011/0238129 | A1 | 9/2011 | Moffitt et al. |
| 2011/0245903 | A1 | 10/2011 | Schulte et al. |
| 2011/0301665 | A1 | 12/2011 | Mercanzini et al. |
| 2011/0313500 | A1 | 12/2011 | Barker et al. |
| 2012/0016378 | A1 | 1/2012 | Pianca et al. |
| 2012/0046710 | A1 | 2/2012 | DiGiore et al. |
| 2012/0071949 | A1 | 3/2012 | Pianca et al. |
| 2012/0165911 | A1 | 6/2012 | Pianca |
| 2012/0197375 | A1 | 8/2012 | Pianca et al. |
| 2012/0203316 | A1 | 8/2012 | Moffitt et al. |
| 2012/0203320 | A1* | 8/2012 | DiGiore et al. ............... 607/148 |
| 2012/0203321 | A1 | 8/2012 | Moffitt et al. |
| 2013/0109254 | A1 | 5/2013 | Klardie et al. |
| 2013/0197424 | A1 | 8/2013 | Bedenbaugh |
| 2013/0197602 | A1 | 8/2013 | Pianca et al. |
| 2013/0261684 | A1 | 10/2013 | Howard |
| 2013/0317587 | A1 | 11/2013 | Barker |
| 2013/0325091 | A1 | 12/2013 | Pianca et al. |
| 2014/0039587 | A1 | 2/2014 | Romero |
| 2014/0039590 | A1 | 2/2014 | Moffitt et al. |
| 2014/0123484 | A1 | 5/2014 | DiGiore et al. |
| 2014/0142671 | A1 | 5/2014 | Moffitt et al. |
| 2014/0155971 | A1 | 6/2014 | Pianca et al. |
| 2014/0180375 | A1 | 6/2014 | Pianca et al. |
| 2014/0358208 | A1* | 12/2014 | Howard et al. ............... 607/116 |
| 2014/0358209 | A1* | 12/2014 | Romero et al. ............... 607/116 |

FOREIGN PATENT DOCUMENTS

| | | | |
|---|---|---|---|
| EP | 0832667 | B1 | 2/2004 |
| EP | 1181947 | B1 | 1/2006 |
| EP | 2092952 | A1 | 8/2009 |
| WO | 9732628 | A1 | 9/1997 |
| WO | 9955411 | A3 | 2/2000 |
| WO | 0038574 | A1 | 7/2000 |
| WO | 0158520 | A1 | 8/2001 |
| WO | 02068042 | A1 | 9/2002 |
| WO | 2004045707 | A1 | 6/2004 |
| WO | 2008018067 | A2 | 2/2008 |
| WO | 2008053789 | A1 | 5/2008 |
| WO | 2008/100841 | A1 | 8/2008 |
| WO | 2009025816 | A1 | 2/2009 |
| WO | 2009102536 | A1 | 8/2009 |
| WO | 2013162775 | A2 | 10/2013 |
| WO | 2014018092 | A1 | 1/2014 |

OTHER PUBLICATIONS

International Search Report and Written Opinion for PCT/US2014/039423 mailed Nov. 11, 2014.
U.S. Appl. No. 14/469,214, filed Aug. 26, 2014.
U.S. Appl. No. 14/286,940, filed May 23, 2014.
U.S. Appl. No. 14/286,889, filed May 23, 2014.
U.S. Appl. No. 14/286,934, filed May 23, 2014.
U.S. Appl. No. 14/325,249, filed Jul. 7, 2014.
U.S. Appl. No. 14/332,212, filed Jul. 15, 2014.
U.S. Appl. No. 14/452,461, filed Aug. 5, 2014.
U.S. Appl. No. 14/286,829, filed May 23, 2014.

* cited by examiner

SEGMENTED ELECTRODE LEADS FORMED FROM PRE-ELECTRODES WITH DEPRESSIONS OR APERTURES AND METHODS OF MAKING AND USING

CROSS-REFERENCE TO RELATED APPLICATIONS

This application claims the benefit under 35 U.S.C. §119 (e) of U.S. Provisional Patent Application Ser. No. 61/829,918, filed May 31, 2013 and U.S. Provisional Patent Application Ser. No. 61/981,606 filed Apr. 18, 2014, both of which are incorporated herein by reference.

FIELD

The invention is directed to the area of electrical stimulation systems and leads and methods of making and using the systems and leads. The present invention is also directed to electrical stimulation leads with segmented electrodes formed from pre-electrodes with exterior depressions or apertures, as well as methods of making and using the segmented electrodes, leads, and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

One embodiment is a pre-electrode for a stimulation lead including a generally cylindrical body having an exterior surface, an interior surface opposite the exterior surface, a proximal end, and a distal end. The body includes segmented electrodes disposed along the body in a spaced-apart configuration. Each of the segmented electrodes having opposing side-walls extending between the proximal end and the distal end of the body. The body also includes connecting material coupling each of the segmented electrodes to one another and forming the exterior surface of the body, cutouts defined between adjacent segmented electrodes, and, for each segmented electrode, a depression in the exterior surface of the pre-electrode over the segmented electrode so that the pre-electrode is thinner at the depression than at immediately adjacent portions of the pre-electrode.

Another embodiment is a pre-electrode for a stimulation lead including a generally cylindrical body having an exterior surface, an interior surface opposite the exterior surface, a proximal end, and a distal end. The body includes segmented electrodes disposed along the body in a spaced-apart configuration. Each of the segmented electrodes having opposing side-walls extending between the proximal end and the distal end of the body. The body also includes connecting material coupling each of the plurality of segmented electrodes to one another, cutouts defined between adjacent segmented electrodes, and at least one aperture extending into the body from the exterior surface and between two of the segmented electrodes. Portions of the connecting material form first and second aperture borders between the aperture and lire proximal and distal ends of the pre-electrode, respectively.

A further embodiment is a method of making a stimulation lead. The method includes disposing any of the pre-electrodes described above along a distal end portion of a lead body; forming a lead body around the pre-electrode; and removing the connecting material from the pre-electrode to release the segmented electrodes.

Another embodiment is a lead formed using one or more any of the pre-electrodes described above to generate segmented electrodes during the manufacture of the lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The invention is directed to the area of electrical stimulation systems and leads and methods of making and using the systems and leads. The present invention is also directed to electrical stimulation leads with segmented electrodes formed from pre-electrodes trades with exterior depressions or apertures, as well as methods of making and using the segmented electrodes, leads, and electrical stimulation systems.

A lead for deep brain stimulation can include stimulation electrodes, recording electrodes, or a combination of both. At least some of the stimulation electrodes, recording electrodes, or both are provided in the form of segmented electrodes that extend only partially around the circumference of the lead. These segmented electrodes can be provided in sets of electrodes, with each set having electrodes radially distributed about the lead at a particular longitudinal position. For illustrative purposes, the leads are described herein relative to use for deep brain stimulation, but it will be understood that any of the leads can be used for applications other than deep brain stimulation, including spinal cord stimulation, peripheral nerve stimulation, or stimulation of other nerves and tissues.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,049,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead can include both recording electrodes and stimulation electrodes or electrodes can be used for both recording and stimulation.

Figure 1:
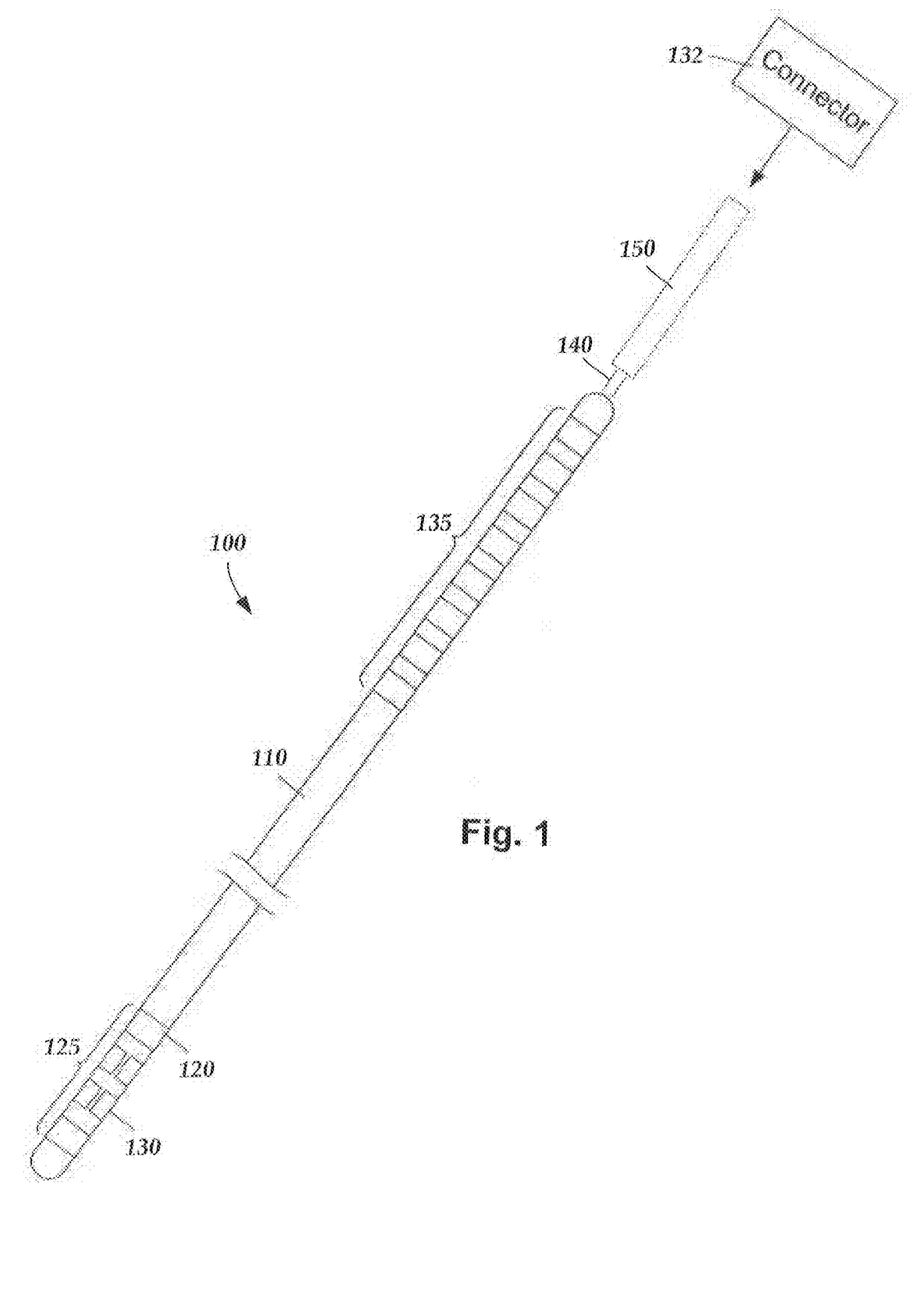
FIG. 1 is a schematic side view of one embodiment of a device for brain stimulation, according to the invention.

FIG. 1 illustrates one embodiment of a device 100 for brain stimulation. The device includes a lead 110, a plurality of electrodes 125 disposed at least partially about a circumference of the lead 110, a plurality of terminals 135, a connector 132 for connection of the electrodes to a control unit and a stylet 140 for assisting in insertion and positioning of the lead in the patient's brain. The stylet 140 can be made of a rigid material. Examples of suitable materials for the stylet include, but are not limited to, tungsten, stainless steel, and plastic. The stylet 140 may have a handle 150 to assist insertion into the lead 110, as well as rotation of the stylet 140 and lead 110. The connector 132 fits over a proximal end of the lead 110, preferably after removal of the stylet 140.

The control unit (not shown) is typically an implantable pulse generator that can be implanted into a patient's body, for example, below the patient's clavicle area. The pulse generator can have eight stimulation channels which may be independently programmable to control tire magnitude of the current stimulus from each channel in some cases the pulse generator can have more or fewer than eight stimulation channels (e.g., 4-, 6-, 16-, 32-, or more stimulation channels). The control unit can have one, two, three, four, or more connector ports, for receiving the plurality of terminals 135 at the proximal end of the lead 110.

in one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the larger neurons are directed to a muscle experiencing tremors, a measurement device can be used to observe the muscle and indicate changes in tremor frequency or amplitude in response to stimulation of neurons. Alternatively, the patient or clinician can observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes typically do not enable stimulus current to be directed from only a limited angular range around of the lead. Segmented electrodes, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead).

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well.

The lead 100 includes a lead body 110, one or more optional ring electrodes 120, and a plurality of sets of segmented electrodes 130. The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Figures 3A, 3B, 3C, 3D:
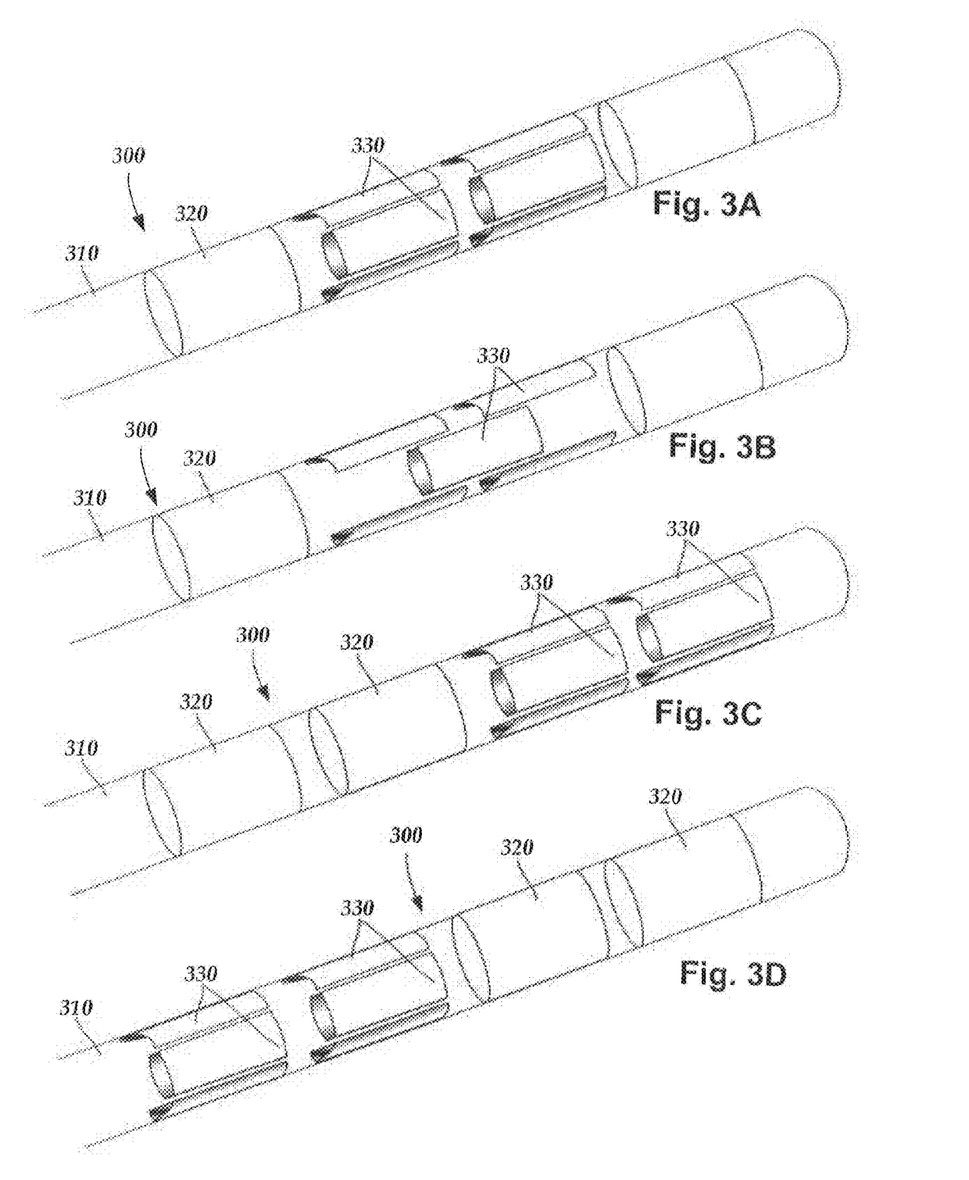
FIG. 3A is a perspective view of an embodiment of a portion of a lead having a plurality of segmented electrodes, according to the invention.
FIG. 3B is a perspective view of a second embodiment of a portion of a lead having a plurality of segmented electrodes, according to the invention.
FIG. 3C is a perspective view of a third embodiment of a portion of a lead having a plurality of segmented electrodes, according to the invention.
FIG. 3D is a perspective view of a fourth embodiment of a portion of a lead having a plurality of segmented electrodes, according to the invention.
Figure 3E:
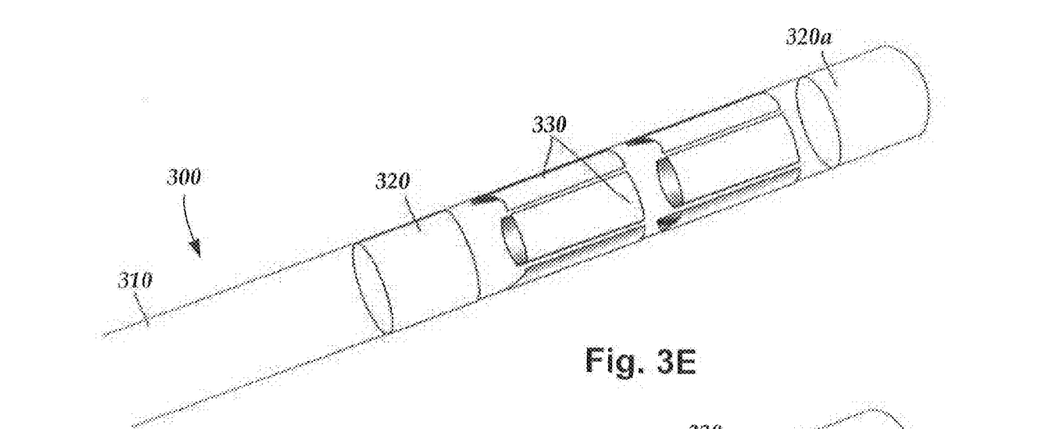
FIG. 3E is a perspective view of a fifth embodiment of a portion of a lead having a plurality of segmented electrodes, according to the invention.

Stimulation electrodes in the form of ring electrodes 120 can be disposed on any part of the lead body 110, usually near a distal end of the lead 100. In FIG. 1, the lead 100 includes two ring electrodes 120. Any number of ring electrodes 120 can be disposed along the length of the lead body 110 including, for example, one, two three, four, five, six, seven, eight, nine, ten, eleven, twelve, thirteen, fourteen, fifteen, sixteen or more ring electrodes 120. It will be understood that any number of ring electrodes can be disposed along the length of the lead body 110. In some embodiments, the ring electrodes 120 are substantially cylindrical and wrap around the entire circumference of the lead body 110. In some embodiments, the outer diameters of the ring electrodes 120 are substantially equal to the outer diameter of the lead body 110. The length of the ring electrodes 120 may vary according to the desired treatment and the location of the target neurons. In some embodiments the length of the ring electrodes 120 are less than or equal to the diameters of the ring electrodes 120. In other embodiments, the lengths of the ring electrodes 120 are greater than the diameters of the ring electrodes 120. The distal-most ring electrode 120 may be a tip electrode (see, e.g., tip electrode 320a of FIG. 3E) which covers most, or all, of the distal tip of the lead.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed, not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Patent Application Publication Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321, all of which are incorporated herein by reference.

The lead 100 is shown having a plurality of segmented electrodes 130. Any number of segmented electrodes 130 may be disposed on the lead body 110 including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body 110. A segmented electrode 130 typically extends only 75%, 67%, 60%, 50%, 40%, 33%, 25%, 20%, 17%, 15%, or less around the circumference of the lead.

The segmented electrodes 130 may be grouped into sets of segmented electrodes, where each set is disposed around a circumference of the lead 100 at a particular longitudinal portion of the lead 100. The lead 100 may have any number segmented electrodes 130 in a given set of segmented electrodes. The lead 100 may have one, two, three, four, five, six, seven, eight, or more segmented electrodes 130 in a given set. In at least some embodiments, each set of segmented electrodes 130 of the lead 100 contains the same number of segmented electrodes 130. The segmented electrodes 130 disposed on the lead 100 may include a different number of electrodes than at least one other set of segmented electrodes 130 disposed on the lead 100.

The segmented electrodes 130 may vary in size and shape. In some embodiments, the segmented electrodes 130 are all of the same size, shape, diameter, width or area or any combination thereof. In some embodiments, the segmented electrodes 130 of each circumferential set (or even ail segmented electrodes disposed on the lead 100) may be identical in size and shape.

Each set of segmented electrodes 130 may be disposed around the circumference of the lead body 110 to form a substantially cylindrical shape around the lead body 110. The spacing between individual electrodes of a given set of the segmented electrodes may be the same, or different from, the spacing between individual electrodes of another set of segmented electrodes on the lead 100. In at least some embodiments, equal spaces, gaps or cutouts are disposed between each segmented electrode 130 around the circumference of the lead body 110. In other embodiments, the spaces, gaps or cutouts between, the segmented electrodes 130 may differ in size or shape. In other embodiments, the spaces, gaps, or cutouts between segmented electrodes 130 may be uniform for a particular set of the segmented electrodes 130, or for all sets of the segmented electrodes 130. The sets of segmented electrodes 130 may be positioned in irregular or regular intervals along a length the lead body 110.

Conductor wires that attach to the ring electrodes 120 or segmented electrodes 130 extend along the lead body 110. These conductor wires may extend through the material of the lead 100 or along one or more lumens defined by the lead 100, or both. The conductor wires couple the electrodes 120, 130 to the terminals 135.

When the lead 100 includes both ring electrodes 120 and segmented electrodes 130, the ring electrodes 120 and the segmented electrodes 130 may be arranged in any suitable configuration. For example, when the lead 100 includes two ring electrodes 120 and two sets of segmented electrodes 130, the ring electrodes 120 can flank the two sets of segmented electrodes 130 (see e.g., FIGS. 1, 3A, and 3E-3H—ring electrodes 320 and segmented electrode 330). Alternately, the two sets of ring electrodes 120 can be disposed proximal to the two sets of segmented electrodes 130 (see e.g., FIG. 3C—ring electrodes 320 and segmented electrode 330), or the two sets of ring electrodes 120 can be disposed distal to the two sets of segmented electrodes 130 (see e.g., FIG. 3D—ring electrodes 320 and segmented electrode 330). One of the ring electrodes can be a tip electrode (see, rip electrode 320a of FIGS. 3E and 3G). It will be understood that other configurations are possible as well (e.g., alternating ring and segmented electrodes, or the like).

By varying the location of the segmented electrodes 130, different coverage of the target neurons may be selected. For example, the electrode arrangement of FIG. 3C may be useful if the physician anticipates that the neural target will be closer to a distal tip of the lead body 110, while the electrode arrangement of FIG. 3D may be useful, if the physician anticipates that the neural target will be closer to a proximal end of the lead body 110.

Figures 3F, 3G:
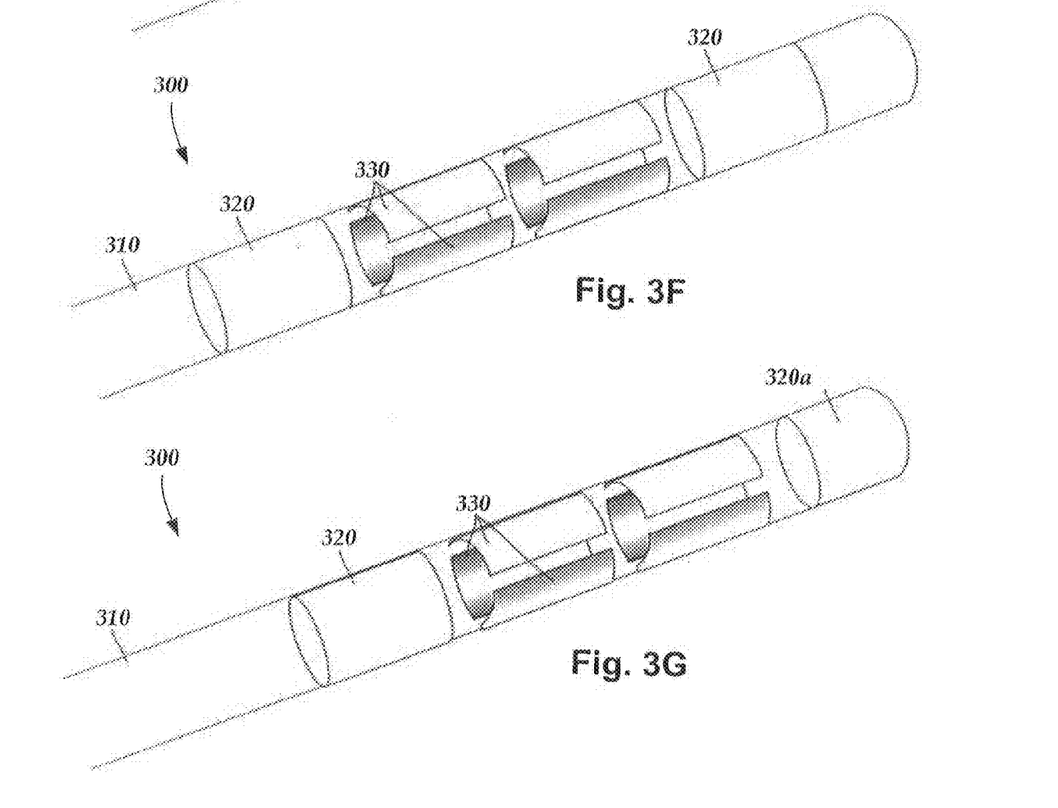
FIG. 3F is a perspective view of a sixth embodiment of a portion of a lead having a plurality of segmented electrodes, according to the invention.
FIG. 3G is a perspective view of a seventh embodiment of a portion of a lead having a plurality of segmented electrodes, according to the invention.

Any combination of ring electrodes 120 and segmented electrodes 130 may be disposed on the lead 100. For example, the lead may include a first ring electrode 120, two sets of segmented electrodes; each set formed of four segmented electrodes 130, and a final ring electrode 120 at the end of the lead. This configuration may simply be referred to as a 1-4-4-1 configuration (FIGS. 3A and 3E—ring electrodes 320 and segmented electrode 330). It may be useful to refer to the electrodes with this shorthand notation. Thus, the embodiment of FIG. 3C may be referred to as a 1-1-4-4 configuration, while the embodiment of FIG. 3D may be referred to as a 1-4-1-1 configuration. The embodiments of FIGS. 3F, 3G, and 3H can be referred to as a 1-3-3-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. The 1-3-3-1 electrode configuration of FIGS. 3F, 3G, and 3H has two sets of segmented electrodes, each set containing three electrodes disposed around the circumference of the lead, flanked by two ring electrodes (FIGS. 3F and 3H) or a ring electrode and a tip electrode (FIG. 3G). In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 2:
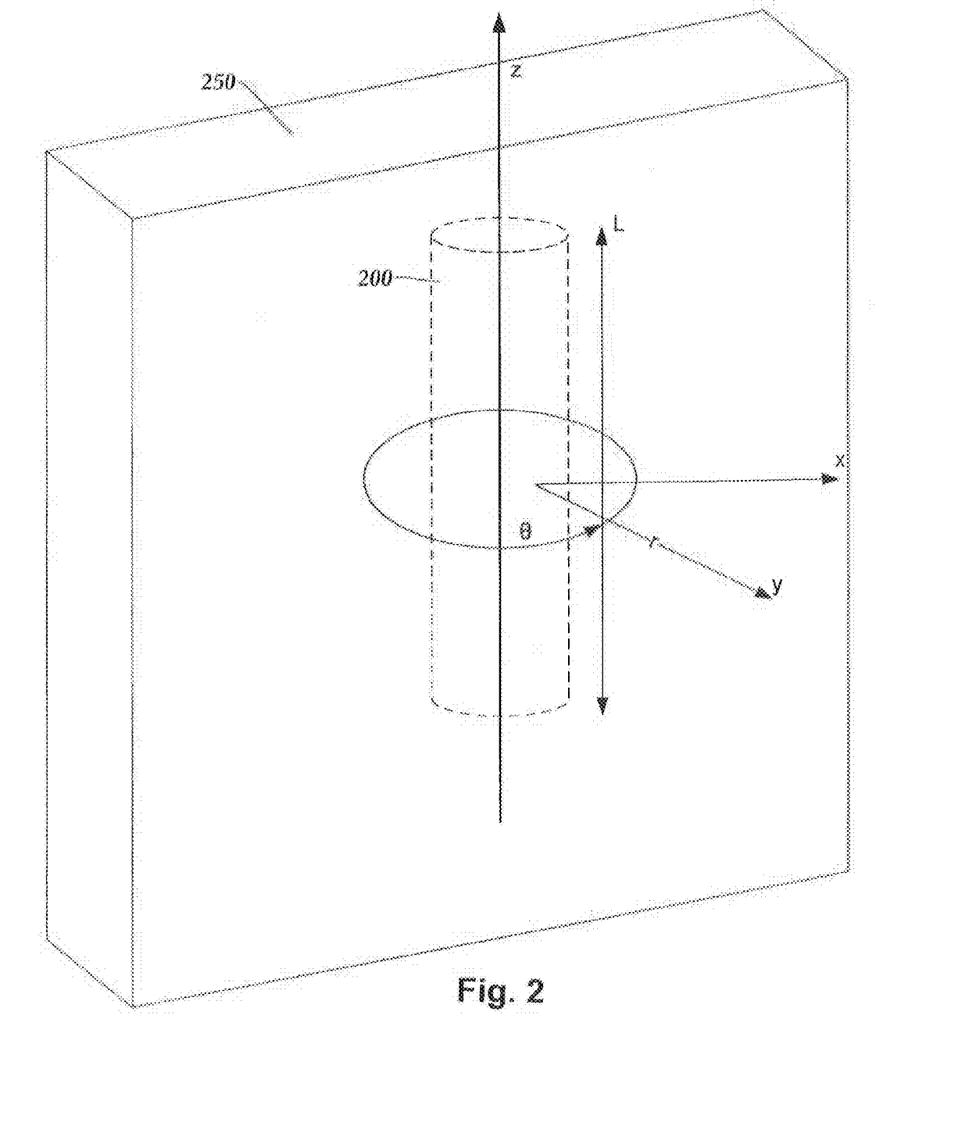
FIG. 2 is a schematic diagram of radial current steering along various electrode levels along the length of a lead, according to the invention.

FIG. 2 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as web as the z-axis. Thus, the centroid of stimulation may be steered in any direction in the three-dimensional space surrounding the lead 200. In some embodiments, the radial distance, r, and the angle θ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 2, the centroid of stimulation can be shifted at each level along the length of the lead 200. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 230 in a set are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

Returning to FIG. 1, when the lead 100 includes a plurality of sets of segmented electrodes 130, it may be desirable to form the lead 100 such that corresponding electrodes of different sets of segmented electrodes 130 are radially aligned with one another along the length of the lead 100 (see e.g., the segmented electrodes 130 shown in FIG. 1). Radial alignment between corresponding electrodes of different sets of segmented electrodes 130 along the length of the lead 100 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 100 are radially aligned with one another and do not radially shift in relation to one another during manufacturing of the lead 100.

In other embodiments, individual electrodes in the two sets of segmented electrodes 130 are staggered (see, FIG. 3B) relative to one another along the length of the lead body 110. In some eases, the staggered positioning of corresponding electrodes of different sets of segmented electrodes along the length of the lead 100 may be designed for a specific application.

Segmented electrodes can be used to tailor the stimulation region so that, instead of stimulating tissue around the circumference of the lead as would be achieved using a ring electrode, the stimulation region can be directionally targeted. In some instances, it is desirable to target a parallelepiped (or slab) region 250 that contains the electrodes of the lead 200, as illustrated in FIG. 2. One arrangement for directing a stimulation field into a parallelepiped region uses segmented electrodes disposed on opposite sides of a lead.

Figure 3H:
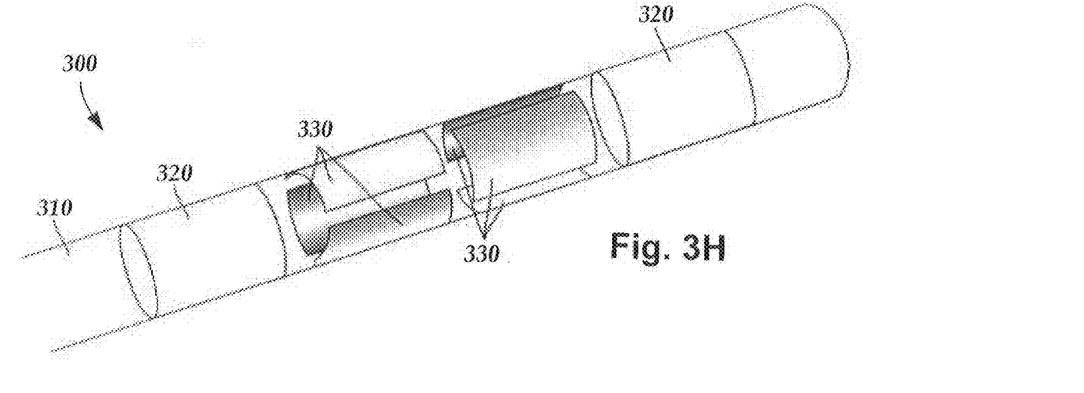
FIG. 3H is a perspective view of an eighth embodiment of a portion of a lead having a plurality of segmented electrodes, according to the invention.

FIGS. 3A-3H illustrate leads 300 with segmented electrodes 330, optional ring electrodes 320 or tip electrodes 320a, and a lead body 310. The sets of segmented electrodes 330 each include either two (FIG. 3B), three (FIGS. 3E-3H), or four (FIGS. 3A, 3C, and 3D) or any other number of segmented electrodes including, for example, three, five, six, or more. The sets of segmented electrodes 330 can be aligned with each other (FIGS. 3A-3G) or staggered (FIG. 3H)

Any other suitable arrangements of segmented electrodes can be used. As an example, arrangements in which segmented electrodes are arranged helically with respect to each other. One embodiment includes a double helix.

One challenge to making leads with segmented electrodes is the correct placement of the electrodes, and retention of the desired electrode placement, during the manufacturing process and after manufacture. Segmented electrodes and methods of manufacture can be designed to address these and other issues. For example, U.S. Provisional Patent Application Ser. Nos. 61/356,529; 61/829,908; 61/829,912; 61/829,918; and 61/870,661, all of which are incorporated herein by reference, as well as other patent applications cited above, provide some examples of segmented electrodes and method of manufacture.

In at least some embodiments a set of segmented electrodes is produced by providing a pre-electrode that is attached to the lead and contains each of the segmented electrodes coupled together by an outer ring of connecting material that is integral with the segmented electrodes. Once the lead body is formed around the pre-electrode, this outer ring is removed to release and separate the individual segmented electrodes.

Sets of radially-disposed segmented electrodes can be formed from pre-electrodes. FIGS. 4A-7 illustrate embodiments of pre-electrodes and sets of segmented electrodes formed from the pre-electrodes (e.g., by grinding down the pre-electrodes to form electrically isolated segmented electrodes). The pre-electrodes, and segmented electrodes formed therefrom, may be formed of an electrical conductor such as a metal, alloy, conductive oxide, or any other suitable conductive material. In some embodiments, the pre-electrodes are formed of platinum, platinum-iridium, iridium, 616L stainless steel (or any other suitable stainless steel), tantalum, Nitinol, iridium rhodium, or a conductive polymer.

In some embodiments, the pre-electrodes are substantially-cylindrical and have a diameter larger than the desired final diameter of a lead. A lead with a cylindrical cross-sectional profile may be obtained by grinding (e.g., center-less grinding), machining, etching, or ablating outer surfaces of the pre-electrodes. The grinding can also release the individual segmented electrodes. In FIGS. 4A-7 three segmented electrodes are shown formed from each pre-electrode. It will be recognized that other embodiments of pre-electrodes can have two, four, five, six, seven, eight, or more segmented electrodes.

Figure 4A:
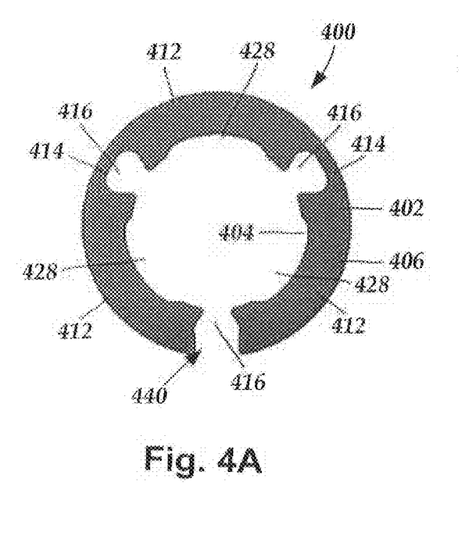
FIG. 4A is a schematic transverse cross-sectional view of one embodiment of a pre-electrode, according to the invention.
Figure 4B:
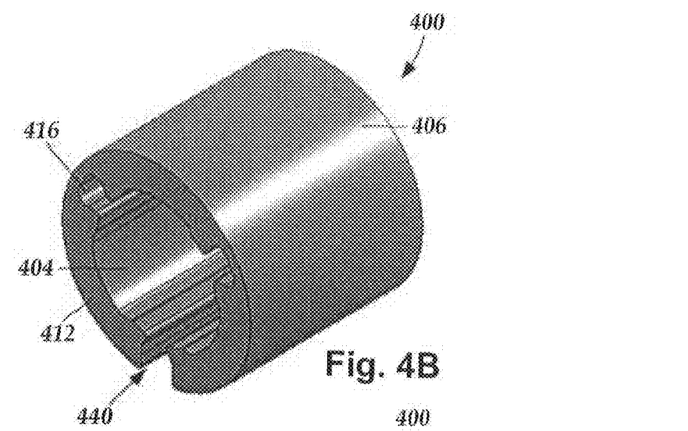
FIG. 4B is a schematic perspective view of the pre-electrode of FIG. 4A, according to the invention.
Figure 4C:
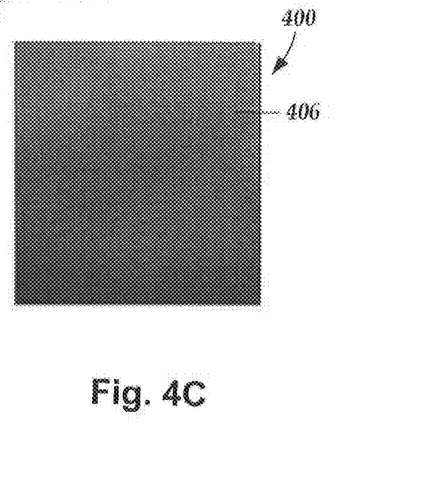
FIG. 4C is a schematic side view of one embodiment of the pre-electrode of FIG. 4A, according to the invention.

FIGS. 4A-4C illustrate one embodiment of a pre-electrode 400 having a body 402 with an interior surface 404 and an exterior surface 406. FIG. 4A is a transverse cross-sectional view of the pre-electrode. FIG. 4B shows a perspective view of the pre-electrode, and FIG. 4C is a side view of the pre-electrode. The body 402 of the pre-electrode 400 is substantially-cylindrical and has a diameter larger than the desired final diameter of a lead upon which the pre-electrode 400 is disposed.

The body 402 defines a slit 440 in the exterior surface 406 that can be used for aligning the pre-electrode 400 visually or aligning the pre-electrode on a corresponding rail, protrusion, or the like in a mold in which the pre-electrode is placed to form the lead body around the pre-electrode. The slit 440 extends the entire longitudinal length of the pre-electrode 400 or at least from one end of the pre-electrode 400. In the embodiment of FIGS. 4A-4C, the slit 440 also extends from the exterior surface 406 of the body 402 to the interior surface 404 of the body. It will be understood, however, that in other embodiments, the slit does not necessarily extend all of the way to the interior surface of the body, but may form a groove in the exterior surface of the body of the pre-electrode.

The pre-electrode has proximal and distal ends defined by fire orientation of the pre-electrode when disposed on a lead. For example, when the pre-electrode is disposed on a lead, the proximal end of the pre-electrode is closest to the proximal end portion of the lead. It will be understood that this orientation of the pre-electrodes, as well as the orientation of the pre-electrodes when disposed on leads, applies to each of the pre-electrodes discussed herein.

The pre-electrode 400 includes individual segmented electrodes 412 joined by connecting material 414. The connecting material 414 can be removed (for example, by grinding, machining, etching, ablating, or otherwise removing the connecting material 414) to leave the separated segmented electrodes 412 when the pre-electrode is in place on the lead.

The pre-electrode 400 defines cutouts 416 between the individual segmented electrodes, which typically define the spacing between the segmented electrodes of a particular set of segmented electrodes. The connecting material 414 corresponds to the material between the segmented electrodes 412 and portions of the pre-electrode 400 disposed over the segmented electrodes. In at least some embodiments, the connecting material 414 forms an outer ring of material that is ground away to release the underlying segmented electrodes. The cutouts can function as lead-retention features by allowing material, such as material from the lead body (including spacers positioned, for example, between sets of segmented electrodes or between a set of segmented electrodes and a ring electrode) or other material, to be placed, or flowed, into the cutouts. The material within the cutouts can also facilitate maintenance of the positioning and spacing of the segmented electrode.

The cutouts 416 have perimeters extending between adjacent portions of the interior surface 404 of the pre-electrode 400. The perimeter can be continuous or discontinuous. Each cutout abuts two segmented electrodes with portions of the perimeter forming side-walls of those segmented electrodes. In at least some embodiments, the perimeter of at least one of the cutouts is shaped such that one or more open cavities (e.g., nooks, notches, voids, indentations, open spaces, or the like or combinations thereof) are formed along at least a portion of the side-wall of at least one of the segmented electrodes abutting that cutout. The cutouts 416 can have a variety of different shapes and arrangements. Examples of other shapes and arrangements for the cutouts 416 can be found in U.S. Provisional Patent Application Ser. Nos. 61/356,529; 61/829,908; 61/829,912; 61/829,918; and 61/870,661, all of which are incorporated by reference.

The pre-electrode 400 further includes one or more channels 428 formed in the segmented electrodes 412. There may be one, two, three, four, or more channels formed in each of the segmented electrodes. The number of channels in each segmented electrode may be the same or different from the number of channels in other segmented electrodes. The channels 428 may be particularly useful for attachment of a conductor to the segmented electrode 412. In at least some embodiments, the one or more channels are defined along the interior surface 404 of the body 402. In FIG. 4A, the one or more channels 428 have arcuate transverse cross-sectional shapes. The channels 428 can have a variety of different shapes and arrangements. Examples of other shapes and arrangements for the channels 428 can be found in U.S. Provisional Patent Application Ser. Nos. 61/356,529; 61/829, 908; 61/829,912; 61/829,918; and 61/870,661, all of which are incorporated by reference.

Figure 5:
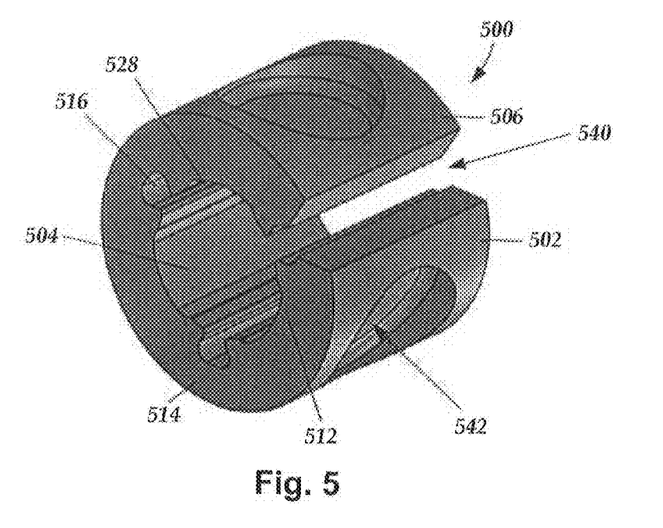
FIG. 5 is a schematic perspective view of a second embodiment of a pre-electrode, according to the invention.

FIG. 5 illustrates another embodiment of a pre-electrode 500 having a body 502 with an interior surface 504 and an exterior surface 506. The pre-electrode 500 also includes segmented electrodes 512 joined by connecting material 514, as well as cutouts 516, channels 528, and a slit 540. All of these elements, and the design considerations for these elements, are the same as the corresponding (similarly named) elements of the embodiment illustrated in FIGS. 4A-4C.

In addition, the pre-electrode 500 includes one or more depressions 542 (also referred to as "pockets") in the exterior surface 506 of the pre-electrode 500. In at least some embodiments, each depression 542 is disposed over one or more of the segmented electrodes 512. In some embodiments, there is a different depression 542 disposed over each of the segmented electrodes 512 of the pre-electrode. The depression 542 can be a dent, dimple, dip, indent, or cutout in the exterior surface 506 of the pre-electrode 500 and may be formed by any suitable method including, but not limited to, molding, cutting, ablation, or the like. The depression 542 can take any shape. In the illustrated embodiment of FIG. 5, the depression 542 has a circular lateral cross-section, but other lateral cross-sectional shapes can be used including square, rectangular, triangular, or other regular or irregular shapes. In the illustrated embodiment, the depression 542 is cylindrical with rounded edges at one end, but other three-dimensional shapes can be used including, but not limited to, cubic, parallelpiped, pyramidal, or other regular or irregular shapes and may or may not have one or more ends with rounded edges.

The depression 542 can facilitate welding of a conductor (not shown) to the interior surface 504 of the pre-electrode 500 or associated segmented electrode 512. The thickness of the pre-electrode 500 at the depression 542 is smaller than adjacent portions of the pre-electrode and may require less heating by a welding instrument to attach the conductor which can aid in speed of manufacture and reduce manufacturing defects or failures.

In at least some embodiments, a depression 542 is disposed over, but does not extend into, the segmented electrode 512. In these embodiments, the depression 542 is disposed entirely within the connecting material 514 that is disposed over the segmented electrode 512 and which will be removed during manufacture to release the individual segmented electrodes. In other embodiments, the depression 542 may extend partway into the segmented electrode 512.

In some embodiments, the one or more depressions 542 in the exterior surface 506 that can be used for aligning the pre-electrode 500 visually or aligning the pre-electrode on a corresponding protrusion or the like in a mold in which the pre-electrode is placed to form the lead body around the pre-electrode.

Figure 6:
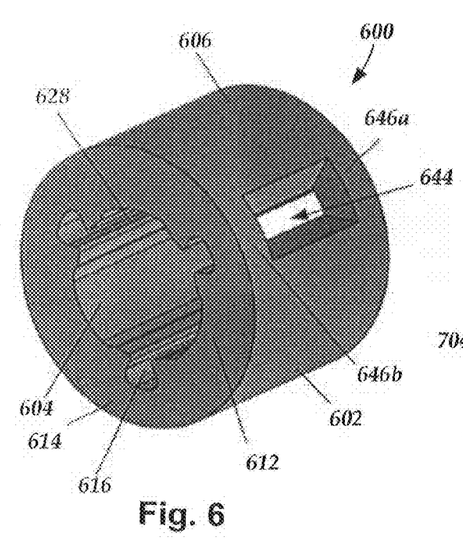
FIG. 6 is a schematic perspective view of a third embodiment of a pre-electrode, according to the invention.

FIG. 6 illustrates another embodiment of a pre-electrode 600 having a body 602 with an interior surface 604 and an exterior surface 606. The pre-electrode 600 also includes segmented electrodes 612 joined by connecting material 614, as well as cutouts 616 and channels 628. All of these elements, and the design considerations for these elements, are the same as the corresponding (similarly named) elements of the embodiment illustrated in FIGS. 4A-4C.

The pre-electrode 600 includes at least one aperture 644 in the exterior surface 606 of the body 602 and extending through the connecting material 614 between segmented electrodes 612. The aperture 644 may align with one of the cutouts 616, as illustrated in FIG. 6.

The aperture 644 does not extend to either of the distal or proximal ends of the pre-electrode 600 in contrast to the slit 440 of pre-electrode 400. A first aperture border 646a and a second aperture border 646b are disposed at respective longitudinal ends of the aperture 644. The first and second aperture borders 646a, 646b are part of the body 602 of the pre-electrode 600 and are formed of the connecting material 614. In at least some embodiments, the aperture 644 extends only through the connecting material. In at least some embodiments, the aperture 644, at the exterior surface 606 of the body 602, is bordered on all sides by connecting material 614, as illustrated in FIG. 6.

In at least some embodiments, it may be advantageous to use an aperture 644 instead of a slit 440 (FIG. 4A) as the pre-electrode 600 will retain its cylindrical shape during manufacture, at least until the connecting material 615 is removed, due, at least in part, to the first and second aperture borders 646a, 646b. In contrast, opposing surfaces of the pre-electrode 400 bordering the slit 440 can further separate, widening the slit 440, during manufacture which may result in defects in the final lead product. In the pre-electrode 600, the first and second aperture borders 646a, 646b prevent the aperture 644 from widening during manufacture.

The aperture 644 in the exterior surface 606 that can be used for aligning the pre-electrode 600 visually or aligning the pre-electrode on a corresponding protrusion or the like in a mold in which the pre-electrode is placed to form the lead body around the pre-electrode. In the embodiment of FIG. 6, the aperture 644 also extends from the exterior surface 606 of the body 602 to the interior surface 604 of the body. It will be understood, however, that in other embodiments, the aperture does not necessarily extend all of the way to the interior surface of the body.

Figure 7:
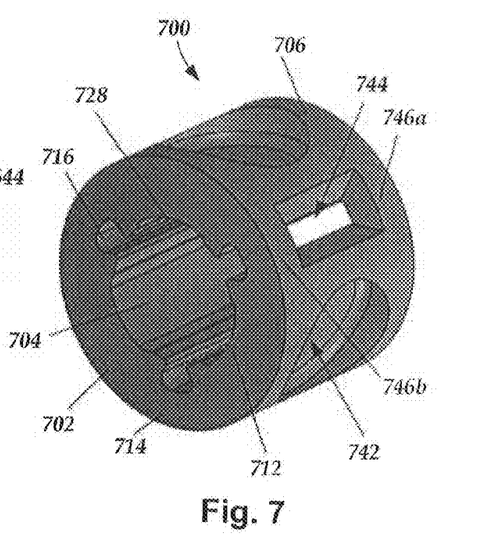
FIG. 7 is a schematic perspective view of a fourth embodiment of a pre-electrode, according to the invention.

FIG. 7 illustrates another embodiment of a pre-electrode 700 having a body 702 with an interior surface 704 and an exterior surface 706. The pre-electrode 700 also includes segmented electrodes 712 joined by connecting material 714, as well as cutouts 716, channels 728, one or more depressions 742, aperture 744, and first and second aperture borders 746a, 746b. All of these elements, and the design considerations for these elements, are the same as the corresponding (similarly named) elements of the embodiment illustrated in FIG. 4A-4C, 5, or 6.

The embodiments illustrated in FIGS. 4A-7 are examples of pre-electrodes. It will be understood, however, that other pre-electrodes can be formed using any combination of depressions, slits, and apertures. For example, the embodiment of FIGS. 4A-4C can be modified to add one or more depressions like depressions 542 of FIG. 5. It will also be understood that other pre-electrodes can be formed using one or more depressions without any slits or apertures. Moreover, one or more depressions (for example, depression 542 of FIG. 5) or one or more apertures (for example, aperture 644 of FIG. 6), or both, can be used in conjunction with other pre-electrode features such as one or more notches, grooves, or the like disposed on the exterior of the pre-electrode as described in U.S. Provisional Patent Application Ser. Nos. 61/356,529; 61/829,908; 61/829,912; 61/829,918; and 61/870,661, all of which are incorporated by reference.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A pre-electrode for a stimulation lead, the pre-electrode comprising:
    a generally cylindrical body comprising an exterior surface, an interior surface opposite the exterior surface, a proximal end, and a distal end, the body comprising
        a plurality of segmented electrodes disposed along the body in a spaced-apart configuration, each of the plurality of segmented electrodes having opposing sidewalls extending between the proximal end and the distal end of the body,
        connecting material coupling each of the plurality of segmented electrodes to one another and forming the exterior surface of the body,
        a plurality of cutouts defined between adjacent segmented electrodes of the plurality of segmented electrodes, and
        for each segmented electrode of the plurality of segmented electrodes, a depression in the exterior surface of the pre-electrode over the segmented electrode so that the pre-electrode is thinner at the depression than at immediately adjacent portions of the pre-electrode, wherein each depression has a circular cross-section.

2. The pre-electrode of claim 1, wherein, for each of the plurality of segmented electrodes, the depression extends into the connecting material, but does not extend into the segmented electrode.

3. A pre-electrode for a stimulation lead, the pre-electrode comprising:
    a generally cylindrical body comprising an exterior surface, an interior surface opposite the exterior surface, a proximal end, and a distal end, the body comprising
        a plurality of segmented electrodes disposed along the body in a spaced-apart configuration, each of the plurality of segmented electrodes having opposing sidewalls extending between the proximal end and the distal end of the body,
        connecting material coupling each of the plurality of segmented electrodes to one another and forming the exterior surface of the body,
        a plurality of cutouts defined between adjacent segmented electrodes of the plurality of segmented electrodes, and
        for each segmented electrode of the plurality of segmented electrodes, a depression in the exterior surface of the pre-electrode over the segmented electrode so that the pre-electrode is thinner at the depression than at immediately adjacent portions of the pre-electrode, wherein each depression has a generally cylindrical shape.

4. The pre-electrode of claim 3, wherein each depression has rounded edges at one end of the generally cylindrical shape.

5. The pre-electrode of claim 1, wherein the pre-electrode comprises a different one of the depressions for each of the segmented electrodes.

6. The pre-electrode of claim 1, further comprising a plurality of conductors, each conductor attached to the interior surface of the body beneath one of the depressions.

7. A method of making a stimulation lead, the method comprising
    disposing the pre-electrode of claim 1 along a distal end portion of a lead body;
    forming a lead body around the pre-electrode; and
    removing the connecting material from the pre-electrode to release the segmented electrodes.

8. The method of claim 7, further comprising prior to removing the connecting material, attaching conductors to the segmented electrodes, wherein each conductor is attached to a portion of the interior surface of the pre-electrode associated with one of the segmented electrodes and opposite one of the depressions.

9. The method of claim 8, wherein attaching conductors to the segmented electrodes comprises welding the conductors to the interior surface of the pre-electrode by applying a welding apparatus to at least one of the depression to weld one of the conductors positioned on the interior surface of the pre-electrode opposite the depression.

10. A pre-electrode for a stimulation lead, the pre-electrode comprising:
    a generally cylindrical body comprising an exterior surface, an interior surface opposite the exterior surface, a proximal end, and a distal end, the body comprising
        a plurality of segmented electrodes disposed along the body in a spaced-apart configuration, each of the plurality of segmented electrodes having opposing sidewalls extending between the proximal end and the distal end of the body,
        connecting material coupling each of the plurality of segmented electrodes to one another and forming the exterior surface of the body,
        a plurality of cutouts defined between adjacent segmented electrodes of the plurality of segmented electrodes, and
        at least one aperture extending into the body from the exterior surface and between two of the segmented electrodes, wherein portions of the connecting material form first and second aperture borders between the aperture and the proximal and distal ends of the pre-electrode, respectively.

11. The pre-electrode of claim 10, wherein the at least one aperture extends through the body from the exterior surface to the interior surface.

12. The pre-electrode of claim 10, wherein the at least one aperture extends only through the connecting material.

13. The pre-electrode of claim 10, wherein at least one of the at least one aperture aligns with a one of the cutouts.

14. The pre-electrode of claim 10, wherein the aperture is configured and arranged for aligning the pre-electrode on a corresponding protrusion in a mold.

15. The pre-electrode of claim 10, wherein the aperture, at the exterior surface of the body, is bordered on all sides by the connecting material.

16. The pre-electrode of claim 10, further comprising, for at least one of the plurality of segmented electrodes, a depression formed in the exterior surface of the pre-electrode over the segmented electrode so that the pre-electrode is thinner at the depression than in immediately adjacent portions of the pre-electrode.

17. The pre-electrode of claim 10, further comprising, for each of the plurality of segmented electrodes, a depression formed in the exterior surface of the pre-electrode over the segmented electrode so that the pre-electrode is thinner at the depression than in immediately adjacent portions of the pre-electrode.

18. A method of making a stimulation lead, the method comprising disposing the pre-electrode of claim 10 along a distal end portion of a lead body;

forming a lead body around the pre-electrode; and removing the connecting material from the pre-electrode to release the segmented electrodes.

19. The method of claim 18, wherein forming the lead body comprises disposing the pre-electrode in a mold using the aperture to align the pre-electrode on a protrusion in the mold.

20. A method of making a stimulation lead, the method comprising disposing the pre-electrode of claim 3 along a distal end portion of a lead body;

forming a lead body around the pre-electrode; and removing the connecting material from the pre-electrode to release the segmented electrodes.

* * * * *